US012029624B2

(12) United States Patent
Benarouch et al.

(10) Patent No.: US 12,029,624 B2
(45) Date of Patent: Jul. 9, 2024

(54) DENTAL DEVICE (71) Applicant: D & D, Paris (FR)

(72) Inventors: Dan Benarouch, Orleans (FR); Delphine Majbruch, Paris (FR)

(73) Assignee: D & D, Paris (FR)

( * ) Notice: Subject to any disclaimer, the term of this patent is extended or adjusted under 35 U.S.C. 154(b) by 653 days.

(21) Appl. No.: 17/045,843

(22) PCT Filed: Apr. 9, 2019

(86) PCT No.: PCT/EP2019/058945
§ 371 (c)(1),
(2) Date: Oct. 7, 2020

(87) PCT Pub. No.: WO2019/197399
PCT Pub. Date: Oct. 17, 2019

(65) Prior Publication Data
US 2021/0137644 A1 May 13, 2021

(30) Foreign Application Priority Data
Apr. 9, 2018 (FR) ...................................... 1853065

(51) Int. Cl.
*A61C 7/10* (2006.01)
*A61C 7/00* (2006.01)
(Continued)

(52) U.S. Cl.
CPC ................ *A61C 7/10* (2013.01); *A61C 7/002* (2013.01); *A61C 7/18* (2013.01); *B33Y 80/00* (2014.12); *A61C 2201/007* (2013.01)

(58) Field of Classification Search
CPC .. A61C 7/10; A61C 7/002; A61C 7/18; A61C 2201/007; B33Y 80/00
See application file for complete search history.

(56) References Cited

U.S. PATENT DOCUMENTS 5,167,499 A * 12/1992 Arndt ...................... A61C 7/00
433/7
5,441,409 A * 8/1995 Tuneberg ................ A61C 7/18
433/23
(Continued)

FOREIGN PATENT DOCUMENTS

WO 2017198640 A1 11/2017

OTHER PUBLICATIONS

International Search Report corresponding to International Application No. PCT/EP2019/058945 dated Jun. 27, 2019, 5 pages.

*Primary Examiner* — Edward Moran
*Assistant Examiner* — Matthew P Saunders
(74) *Attorney, Agent, or Firm* — Ronald M. Kachmarik; Cooper Legal Group LLC (57) ABSTRACT

Method for manufacturing a dental expander having a first attachment member intended to be fixed to a first fixation tooth of a patient and an active member rigidly connected to the first attachment member. The method includes: a) generating a three-dimensional digital model of a dental arch having the fixation tooth or "arch model"; b) using the arch model as a basis for generating: a three-dimensional digital model of the first attachment member, wherein the model of the first attachment member that has an inner surface that substantially reproduces a part of the surface of the first fixation tooth, and/or a three-dimensional digital model of the active member; and c) using the model of the first attachment member as a basis for manufacturing the first attachment member and/or using the model of the active member as a basis for generating the active member.

17 Claims, 2 Drawing Sheets

(51) Int. Cl.
*A61C 7/18* (2006.01)
*B33Y 80/00* (2015.01)

(56) References Cited

U.S. PATENT DOCUMENTS

| | | | |
|---|---|---|---|
| 10,945,818 B1* | 3/2021 | Motlagh | A61C 7/08 |
| 2003/0124480 A1* | 7/2003 | Peacock, III | A61C 7/18 |
| | | | 433/23 |
| 2005/0186524 A1* | 8/2005 | Abolfathi | A61C 7/10 |
| | | | 433/7 |
| 2006/0093982 A1* | 5/2006 | Wen | A61C 7/08 |
| | | | 433/6 |
| 2016/0081768 A1* | 3/2016 | Kopelman | A61C 7/10 |
| | | | 433/6 |
| 2016/0081769 A1* | 3/2016 | Kimura | A61C 7/002 |
| | | | 433/7 |
| 2017/0007367 A1* | 1/2017 | Li | G06Q 30/0621 |
| 2017/0079747 A1* | 3/2017 | Graf | A61C 7/002 |
| 2018/0153648 A1* | 6/2018 | Shanjani | B33Y 50/02 |
| 2019/0152152 A1* | 5/2019 | O'Leary | B33Y 50/00 |

* cited by examiner

Fig. 1a  Fig. 1b  Fig. 1c

| generating a dental model of the fixation tooth |
| generating a ring model on the basis of the dental model |
| manufacturing a ring on the basis of the ring model |
| treating the surface of the ring |
| fixing a connecting member to said ring |

DENTAL DEVICE

TECHNICAL FIELD

The invention relates to a dental device, a dental fixation ring, and a method for manufacturing such a ring and such a dental device.

PRIOR ART

A dental device is intended to be fixed to the teeth of a patient. To this end, it has one, two or more than two bracket members, each bracket member being fixed rigidly, for example adhesively bonded, to a tooth referred to as a "fixation tooth".

It also has an active member which is connected to the bracket members and which has the function of exerting an action on the one or more fixation teeth, generally in order to move them relative to each other. The action can be a pulling action, for example.

The bracket members are typically chosen from among dental fixation rings and orthodontic brackets.

Figure 1A:
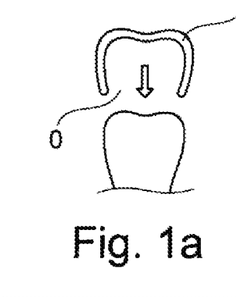
FIG. 1 is a schematic illustration of the different steps involved in fixing a ring according to the prior art.
Figure 1B:
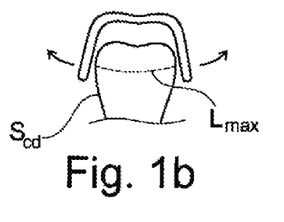
Figure 1C:
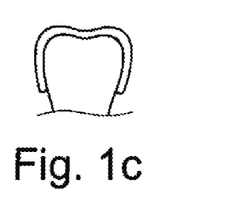

A dental fixation ring is a shell traditionally intended to be fixed to a molar by means of a glue or a sealing cement. To this end, the ring traditionally has an elastic deformability allowing it to be clipped onto the fixation tooth. More precisely, as is illustrated in FIG. 1a, the ring 1 defines an opening O whose dimensions permit only a force-fit engagement on the fixation tooth. As is illustrated in FIG. 1b, during the engagement on the fixation tooth, the edge defining the opening deforms in order to increase the surface area of said opening as far as the passage of the line of greatest contour $L_{max}$ of the tooth. After passing this line, this edge returns elastically to its original position, bearing on an undercut surface $S_{cd}$ of the fixation tooth, which maintains the ring in position on this tooth (FIG. 1c).

An orthodontic bracket is intended, like the ring, to be fixed, traditionally adhesively bonded, to a tooth. In contrast to a ring, an orthodontic bracket does not form a shell encircling the fixation tooth.

An orthodontic bracket is generally fixed to an incisor, a canine or a premolar, preferably to the vestibular or lingual aspect of the teeth.

A ring can complement a multi-bracket device in the posterior sectors. The masticatory forces exerted in the posterior sectors increase the probability of detachment. Since the rings detach less easily than the orthodontic brackets, it is preferable to combine rings in the posterior sector and orthodontic brackets on the premolars, canines and incisors.

There is a permanent need for a dental device better adapted to the needs of the patient and thus permitting more effective treatment.

There is also a need for a method of manufacturing a dental device in a way that limits the number of visits to the orthodontist, especially for designing and trying out the prototypes of the bracket members, especially rings.

There is lastly a need for a method of manufacturing a dental device in a way that limits the pain experienced by the patient during the preparation of this dental device.

It is an object of the invention to meet these needs, at least partially.

SUMMARY OF THE INVENTION

The invention proposes a method for manufacturing a dental device having:

a first bracket member intended to be fixed to a first fixation tooth of a patient;
an active member rigidly connected to the first bracket member;
said method having the following successive steps:
a) a three-dimensional digital model of a dental arch having the fixation tooth, or "arch model", is generated, preferably by means of an optical scanner, an X-ray scanner or cone beam CT, preferably by means of an optical scanner;
b) the arch model and preferably a treatment to be applied to the patient are used as a basis for generating:
a three-dimensional digital model of the first bracket member, the model of the first bracket member having an inner surface that substantially reproduces a part of the surface of the first fixation tooth, and/or
a three-dimensional digital model of the active member;
c) the model of the first bracket member is used as a basis for manufacturing said first bracket member, and/or the model of the active member is used as a basis for manufacturing said active member, in each case preferably by 3D printing;
d) the bracket member is preferably treated in such a way that its inner surface has a roughness greater than the roughness of its outer surface.

Preferably, in step c), a computer is used to simulate the action of a dental device manufactured on the basis of the model of the first bracket member and/or the model of the active member, in order to define
the shape and/or the orientation of a groove of the first bracket member, and/or
the shape and/or the constituent material of the active member, and/or
the shape of a second bracket member.

Preferably, a basal, alveolar or dental correction is simulated for the patient.

The first bracket member, preferably printed by 3D printing, can be an orthodontic bracket or a dental fixation ring having a bottom intended to be placed on an occlusal surface of the first fixation tooth, and a lateral wall intended to encircle said first fixation tooth, the lateral wall being composed of a lingual wall, a vestibular wall and first and second proximal walls.

The first bracket member is preferably made of a material chosen from among the alloys of cobalt-chromium, titanium, the alloys of nickel-titanium and the alloys of titanium-niobium.

The active member can be made integral with the first bracket member or can be attached thereto, generally after fixation of the bracket member.

The dental device preferably has at least first and second bracket members, and an active member which extends between the two bracket members. The active member can thus be a crosspiece or a connecting member depending on whether it is formed integrally with at least one bracket member, in such a way as to form, or not to form, a one-piece assembly. In other words, the connecting member is independent of the bracket members before being fixed thereto. A crosspiece can also be independent of a bracket member before being fixed thereto, but it forms a one-piece assembly with at least one bracket member.

The connecting member can be put in place in order to be fixed to the bracket members, generally after these bracket members have been fixed to the teeth, respectively. The connecting member is then initially independent of the bracket members.

The connecting member can be, for example, an orthodontic archwire, for example with shape memory, which slides in grooves or sheaths formed in bracket members.

Preferably, when it serves for the fixation of a connecting member, a bracket member has a fastener for this purpose. The bracket can in particular have a groove in which the connecting member is arranged before being immobilized.

The connecting member can also be welded to the first bracket member, which is particularly advantageous when the connecting member is made to measure.

The active member is preferably chosen from:
- a crosspiece connecting the first bracket member to a second bracket member intended to be fixed to a second fixation tooth of the patient;
- a connecting member for connecting the first bracket member to a second bracket member, the connecting member being intended to be placed on and fixed to the first bracket member, in particular an orthodontic archwire, for example a Delaire double archwire, a transpalatal archwire or a lingual archwire.

Preferably, the connecting member is made of a shape-memory material. In one embodiment, it has an actuator.

Preferably, the connecting member is made to measure, preferably by a prosthetist, or is obtained by folding of a preformed member, preferably by an orthodontist.

When the active member is a connecting crosspiece, the second bracket member is preferably formed integrally with the first bracket member and preferably with the connecting crosspiece, that is to say it forms with them a one-piece assembly that is manufactured simultaneously, preferably by 3D printing.

The invention relates in particular to a one-piece multi-bracket dental device manufactured by 3D printing, having a plurality of bracket members and a connecting crosspiece forming a one-piece assembly with the bracket members, in which device the bracket members and the connecting crosspiece are defined according to the action that is to be exerted specifically on the teeth of the patient.

Connecting several teeth to one another can advantageously serve to ensure dental anchoring and to avoid any undesired movement of the teeth.

Moreover, the traditional multi-bracket dental devices intended for retraction of a group of teeth or for intermaxillary traction or for disinclusion of a tooth ensure anchoring through the use of steel orthodontic archwires of large cross section, which often requires leveling of the dental arch. With a one-piece multi-bracket dental device according to the invention, it is advantageously possible to omit the leveling step. The duration of the orthodontic treatment is thus reduced.

The second bracket member is preferably manufactured in step c), preferably by 3D printing, on the basis of a model of the second bracket member generated in step b) and having an inner surface that substantially reproduces a part of the surface of the second fixation tooth.

The dental device can have an accessory preferably chosen from:
- a fastener for first fixation member, for the fixation of a connecting member; and/or
- a hook for fastening an intermaxillary elastic traction device;
- a sheath for passage of a connecting member, which sheath can be vestibular or lingual;
- a spacer;
- a vestibular abutment.

The accessory is preferably formed integrally with the first bracket member so as to form a one-piece assembly.

According to a first main variant of the method according to the invention, the active member is made of a shape-memory material, preferably chosen from the alloys of cobalt-chromium, titanium, the alloys of nickel-titanium and the alloys of titanium-niobium.

The shape of the active member and the shape-memory properties are preferably determined according to the treatment that is to be applied to the patient.

The inventors have discovered that the method according to the first main variant of the invention allows the dental device an action that is perfectly targeted to the needs of the patient.

The 3D printing also permits rapid manufacture and enables specific configurations.

Preferably, the shape memory of the active member is deactivated, traditionally by cooling, before the active member is fixed in the mouth of the patient. The body temperature then reactivates the shape memory, which allows the dental device to apply the intended action, preferably a continuous and individually tailored action.

Preferably, the bracket members and the active member form a one-piece assembly, preferably manufactured using a shape-memory alloy. Preferably, however, a heat treatment is applied to the bracket members in order to suppress their shape memory.

According to a second main variant of the method according to the invention, the method entails, in step c), the formation of a groove in the first bracket member, such that the active member can be fixed rigidly there.

Preferably, the orientation of the groove is defined according to the action that is to be exerted on the patient's teeth specifically by the active member.

Preferably, a computer is used to simulate an alveolar/dental correction for the patient, in order to define the shape and/or the orientation of the groove.

After said groove has been formed, said active member is placed in said groove and is then immobilized in said groove.

The inventors have discovered that the method according to the second main variant of the invention allows the dental device an action that is perfectly targeted to the needs of the patient. In addition, the active member can advantageously be a conventional connecting member.

The invention relates in particular to a multi-bracket dental device manufactured by 3D printing, having a plurality of bracket members and an active member, in which device the bracket members have grooves for receiving the active member, which grooves are defined according to the action that is to be exerted on the teeth of the patient specifically by the active member, one or more of the bracket members being able alternatively to be manufactured, by 3D printing, at the same time as the active member.

Such a multi-bracket dental device has the same advantages as a one-piece multi-bracket device according to the invention as described above. In addition, the use of an active member in the form of a removable connecting member affords the possibility of removing the connecting member when its action is completed, in order to replace it with another connecting member that exerts a different action, without having to remove the bracket members.

Finally, when the dental device has a plurality of active members, including at least one connecting member, for example for ensuring simultaneously an action of palatal expansion and an action of alignment of the teeth, the change of the connecting member does not substantially modify the action of the one or more other active members. For example, the aligning action of an active member is advantageously not substantially affected when a connecting member acting on the palatal expansion is replaced by a connecting member that is passive with respect to the palatal expansion.

According to a third main variant of the method according to the invention, the first bracket member is a ring and, in step b), the ring model is defined in such a way that the ring resulting from step c):

does not extend on a zone of contact of the fixation tooth with an adjacent tooth, when the ring is in a service position in which it is fixed to the fixation tooth; and/or does not have an undercut surface, that is to say bearing, in the service position, on an undercut surface of the first fixation tooth; and/or does not extend, in the service position, beyond the line of greatest contour of the first fixation tooth or, preferably, extends beyond the line of greatest contour of the first fixation tooth without defining an undercut region.

The inventors have discovered that the method according to the third main variant of the invention allows the ring to be positioned on the first fixation tooth without having to push back the one or more teeth adjacent to the fixation tooth, and without compressing the surface of the first fixation tooth in proximity to the line of greatest contour. Thus, the ring better complies with the anatomy of the first fixation tooth.

The absence of an undercut surface of the ring, in contrast to normal practice, advantageously permits fixation of the ring without clipping, that is to say without it being necessary for the ring to bear on the undercut surfaces of the first fixation tooth.

The inventors have finally established that, after the adhesive bonding, the ring is advantageously fixed in a very reliable manner.

According to a fourth main variant of the method according to the invention, the first bracket member is a ring and, in step b), the ring model is defined in such a way that the ring has a bottom through which at least one hole extends.

The bottom of the ring is intended to rest on the occlusal surface of the first fixation tooth. The formation of a hole in the bottom of the ring advantageously limits the interactions between the ring and the antagonist tooth with respect to the fixation tooth.

The inventors have found that the risk of detachment of the ring is greatly reduced by this means. In addition, the ring is better accepted by the patient.

Preferably, the hole is defined in such a way that, in the service position, the bottom of the hole does not even partially cover the mastication surface of the fixation tooth.

According to a fifth main variant of the method according to the invention, the first bracket member is a ring and the method comprises, after step c), a step d) in which the surface of the ring is treated. Preferably, at step d), at least part of the outer surface of the ring is polished, without the inner surface of the ring being polished.

As will be seen in more detail in the description below, the roughness of the inner surface of the ring, greater than that of the outer surface, enhances the efficacy of the fixation of the ring on the fixation tooth.

Of course, the different characteristics, whether optional or not, of the different main variants of the invention can be combined.

Irrespective of the main variant under consideration, a method according to the invention can also comprise one or more of the following optional features:

the active member has or preferably consists of a shape-memory material or of a polymer and/or ceramic material deformable under the effect of a stimulus, preferably under the effect of a temperature increase resulting from the expander being placed in the service position;

after step c), the shape memory of the active member is deactivated by cooling before the expander is fixed in the service position in the mouth of the patient, the shape-memory material being chosen such that the body temperature of the patient reactivates said shape memory;

in step c), the active member is preferably made integral with the first and/or second bracket member so as to form a one-piece assembly;

in step c), the active member is manufactured from a material identical to that of the first bracket member and/or of the second bracket member;

in step d), at least part of the outer surface of the bracket member is polished, without the inner surface of the first bracket member being polished;

the first bracket member is a ring and, in step b), the ring model is defined in such a way that the height of the lingual wall and/or of the vestibular wall is greater than the height of the first proximal wall and/or of the second proximal wall;

the first bracket member is a ring and, in step b), the ring model is defined in such a way that the lingual wall and/or the vestibular wall extend, from the bottom, beyond the line of greatest contour of the fixation tooth;

the first bracket member is a ring and, in step b), when the first proximal wall is intended to extend, in the service position, between the first fixation tooth and an adjacent tooth in contact with the first fixation tooth via a contact zone, the ring model is defined in such a way that, in said service position, the first proximal wall does not reach said contact zone.

In one embodiment, in step c), a dental device is manufactured, preferably by 3D printing, having an assembly of bracket members, preferably an active member connecting bracket members of said assembly, and a support keeping said bracket members in relative positions corresponding to their relative positions in a service position in which said bracket members are fixed to respective fixation teeth.

The support is preferably configured to permit indirect adhesive bonding of the dental device. Advantageously, the positioning in the service position and the adhesive bonding are thereby simplified.

In one embodiment, the support is detachable after the bracket members have been fixed to the teeth.

In another embodiment, it is not detachable and therefore remains present during the treatment of the patient.

The invention also relates to a dental device manufactured by a method according to the invention.

The dental device can in particular be chosen from among an expander, a retractor and a thumb guard.

The invention is adapted in particular to an expander. In particular, the actuator of the conventional expanders, used to laterally widen the expander, is preferably replaced by an active member manufactured according to the invention, preferably made of a shape-memory material. The active member then acts as a spring.

The expansion of the palate can thus be individually customized, the degree of expansion being determined in advance by computer, in such a way as to manufacture an active member adapted to provide this degree of expansion.

The expander is advantageously fixed, and the expansion takes place without any specific action on the part of the patient.

Definitions

The "mastication surface" is the surface via which the fixation tooth comes into contact with one or more teeth of the antagonist arch during mastication, in the absence of a ring.

A "fixation" is a "definitive" connection, that is to say one that does not permit deliberate disconnection by the patient, in contrast to an orthodontic aligner for example.

An "arch model" is understood as a model representing all or part of said arch.

The "line of greatest contour" is the expression traditionally used for the line which defines the greatest contour of a tooth, a contour being a line extending on an outer surface of the tooth, in a plane transverse to the X axis of the tooth, and encircling the tooth.

BRIEF DESCRIPTION OF THE FIGURES

Further features and advantages of the invention will become clear from reading the following detailed description and examining the attached drawing, in which.

DETAILED DESCRIPTION

Figure 2:
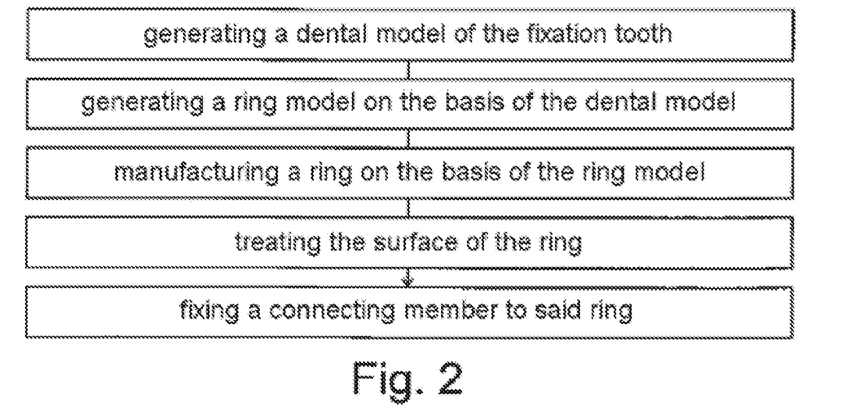
FIG. 2 shows schematically a method according to the invention.
Figure 3:
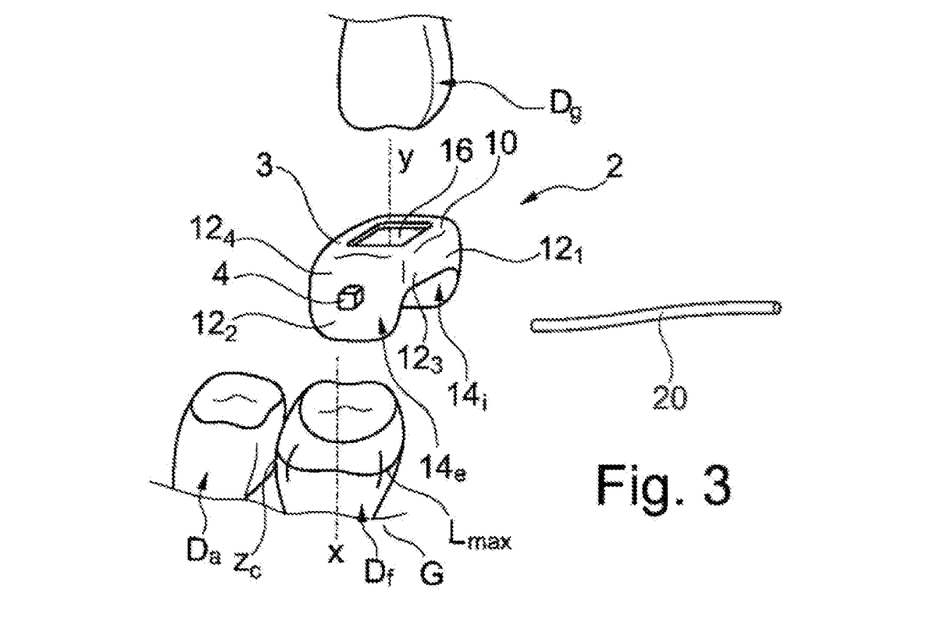
FIG. 3 shows schematically the fixation of a ring according to the invention.

Since FIG. 1 has been described in the preamble, reference is now made to FIGS. 2 and 3.

A ring 2 according to the invention has a shell 3 provided with a ring fastener 4 permitting the fixation of a connecting member which, in the service position, exerts a force on a fixation tooth $D_f$ on which the fixation ring 2 is affixed.

The ring 2 has a bottom 10, or "occlusal wall", intended to bear on the occlusal surface of the fixation tooth, and a lateral wall 12 extending, in the service position, from the bottom 10 toward the gum G. The bottom 10 has a hole 16 passing through it, the hole 16 being adapted such that, in the service position, the mastication surface of the fixation tooth can come into contact with an antagonist tooth $D_g$.

The hole 16 is preferably defined in such a way that, in the service position, the bottom of the ring does not even partially cover the mastication surface of the fixation tooth. The surface area of the hole 16 is preferably greater than 0.5 times, preferably greater than 0.8 times, preferably greater than 1.0 time and/or less than 1.2 times, preferably less than 1.1 times the surface area of the mastication surface of the fixation tooth. The limitation of the surface area of the hole advantageously allows the inner surface of the ring to ensure effective fixation on the fixation tooth.

The lateral wall 12 is composed of a lingual or palatal wall $12_1$ extending, in the service position, opposite the tongue, a vestibular wall $12_2$ opposite the lingual wall $12_1$ and facing, in the service position, the cheeks and/or lips, and first and second proximal walls $12_3$ and $12_4$, at least one of the proximal walls separating, in the service position, the fixation tooth and an adjacent tooth $D_a$.

The "height" of a wall is the dimension of this wall, measured along the Y axis of the ring, from the bottom 10 of the ring. Preferably, the height of the lingual wall $12_1$ and/or of the vestibular wall $12_2$ is greater than the height of the first proximal wall and/or of the second proximal wall. Preferably, the height of the lingual wall $12_1$ and/or of the vestibular wall $12_2$ is greater than 1 mm and/or less than 15 mm. Preferably, the height of the first proximal wall and/or of the second proximal wall is greater than 0.5 mm and/or less than 10 mm.

Preferably, the heights of the lingual and vestibular walls are substantially identical. The same applies to the proximal walls.

However, the lingual wall $12_1$ and/or the vestibular wall $12_2$ preferably extend from the bottom 10 in such a way that, in the service position, they do not extend beyond the line of greatest contour $L_{max}$ of the fixation tooth.

Preferably, when a proximal wall is intended to extend between the fixation tooth $D_f$ and an adjacent tooth $D_a$ in contact with the fixation tooth via a contact zone $Z_c$, the height of this proximal wall is determined in such a way that, in the service position, it does not reach the contact zone $Z_c$. The fixation of the ring 2 does not therefore necessitate forcing a passage between the fixation tooth $D_f$ and the adjacent tooth $D_a$.

The bottom 10 and the lateral wall 12 together form a basin which defines the inner surface $14_i$ of the ring, oriented toward the interior of the basin, and the outer surface $14_e$, oriented toward the outside of the basin.

At least part, preferably all, of the inner surface $14_i$ is preferably rough to the touch, which optimizes the efficacy of the adhesive bonding of the ring 2.

At least part, preferably all, of the outer surface $14_e$ is preferably smooth to the touch, preferably polished, which improves the appearance of the ring.

The ring fastener 4 can be of any desired type. It preferably has the shape of a stirrup configured such that, in a passive position, it can receive a connecting member 20 and, in an active position, it can clamp the connecting member so as to hold the latter in position.

Traditionally, during orthodontic treatment, the connecting member 20 is fixed to two rings. It can be active and in particular can be configured to exert a force that tends to bring the two rings closer or to space them apart from each other. The objective may be to move one and/or both of the fixation teeth that are thus joined by the connecting member. It can also be passive in order to maintain the relative positions of the fixation teeth.

The connecting member can be in particular an orthodontic archwire with shape memory or a spring with shape memory or an actuator.

A ring according to the invention can in particular be manufactured according to the steps described above, in particular according to the preferred embodiment described below.

A ring according to the invention can moreover be provided with:
- a crosspiece for connecting to another ring or to an orthodontic bracket;
- a hook for fastening an intermaxillary elastic traction device;
- a sheath for passage of an orthodontic archwire;
- a spacer;
- a vestibular abutment, useful during the placement of the ring.

A ring according to the invention is preferably manufactured together with the one or more accessories, so as to form a one-piece dental device.

Figure 4A:
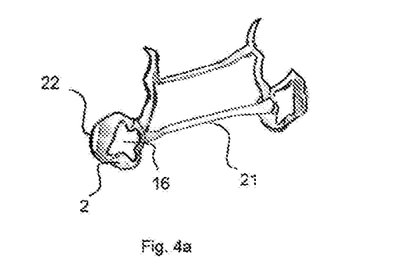
FIGS. 4a-4e show examples of dental devices having a ring according to the invention.
Figure 4B:
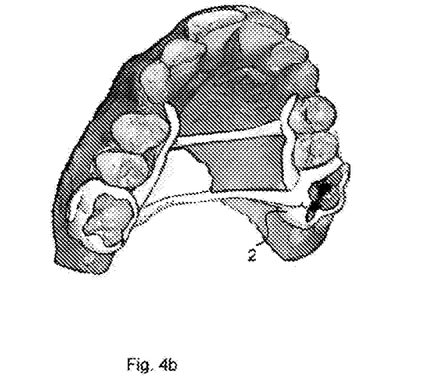

FIG. 4a shows an example of a dental device according to the invention, in this case an expander, having two rings 2 connected by two connecting crosspieces 21 which follow the shape of the dental arch. The rings carry hooks 22. FIG. 4b shows this device in its service position.

Figure 4C:
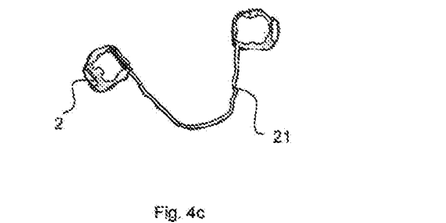

FIG. 4c shows a dental device according to the invention, in this case a lingual archwire, having two rings 2 connected by a connecting crosspiece 21 which follows the contour of the arch. This device can be fixed to a lower arch.

Figure 4D:
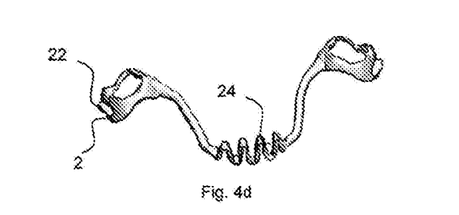

FIG. 4d shows a dental device according to the invention having two rings 2 connected by a connecting crosspiece 21 which carries a thumb guard 24.

Figure 4E:
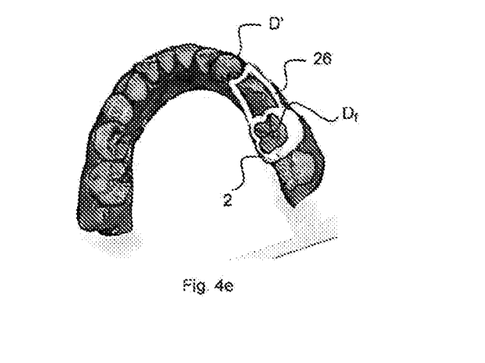

FIG. 4e shows a dental device according to the invention, in this case a retractor, having a ring 2 fixed to a fixation tooth $D_f$ and provided with a spacer 26 bearing on a support tooth $D^t$ of the same arch, so as to keep the fixation tooth and the support tooth spaced apart from each other. The spacer 26 preferably has an annular shape.

A spacer has the function of avoiding any version of teeth adjacent to an edentulous zone, a future space for eruption of a tooth.

All of these are one-piece devices and are each manufactured in a single operation by means of 3D printing.

In a preferred embodiment, one or more orthodontic brackets are manufactured by 3D printing, preferably at the same time as the ring.

An orthodontic bracket can be connected to a ring according to the invention by a connecting crosspiece, with the assembly of ring, connecting crosspiece and orthodontic bracket forming a one-piece assembly. This embodiment is particularly useful for improving dental anchoring in the context of retraction of the teeth of the incisor/canine block, or for using intermaxillary elastics without having to use a traditional multi-bracket appliance and especially without having to level and align the teeth in advance. The resulting saving in time is considerable.

An orthodontic bracket can be connected to a ring according to the invention by a connecting member. In a multi-bracket appliance, the connecting member is an orthodontic archwire.

The method is described below in the context of the manufacture of a ring.

In step a), the orthodontist takes a scan of the dental arch comprising the fixation tooth $D_f$ so as to generate an "arch model". All conventional optical scanners can be used.

Preferably, the model of the dental arch comprising the fixation tooth $D_f$ is then segmented in order to generate a three-dimensional digital model of the fixation tooth, or a "dental model". In one embodiment, the arch model serves as dental model.

Preferably, the orthodontist also takes a scan of the antagonist tooth $D_a$, preferably the antagonist arch, which allows him to determine the occlusion position and thereby determine the mastication surface of the fixation tooth. The mastication surface can also be determined by the optical impression of the dental arches in occlusion. The mastication surface can also be individualized by use of dynamic modeling systems (for example from the company Modjaw).

In step b), the dental model is analyzed in order to design a three-dimensional digital model of a ring according to the invention, or "ring model", defining an inner surface identical to the outer surface of the fixation tooth.

The operator is preferably a company specialized in the design and manufacture of the rings. It preferably works for a number of orthodontists, preferably more than 100, more than 1,000 or more than 10,000 orthodontists.

Preferably, the operator determines the line of greatest contour $L_{max}$ of the fixation tooth. The arch model also allows the operator to determine the one or more possible contact zones $Z_c$ that the fixation tooth has with the adjacent teeth.

Knowing the one or more contact zones $Z_c$, the line of greatest contour $L_{max}$ and the mastication surface of the fixation tooth, the operator then models the ring 2 such that, in its service position, its inner surface $14_i$ closely matches the surface of the fixation tooth, without extending beyond the line of greatest contour $L_{max}$, and without reaching the one or more contact zones Zc. Preferably, the operator creates a ring model comprising a hole whose dimensions and position are defined such that the ring does not cover the mastication surface of the fixation tooth. Any of the traditional modeling techniques can be used for this purpose.

This form of the ring model avoids the clipping of the ring manufactured in step c) onto the fixation tooth while at the same time facilitating its placement in the service position, then its acceptance by the patient.

Preferably, the ring model is determined in such a way that at least one of the lingual and vestibular walls of the ring, preferably each of these walls, extends toward the gum in the service position, substantially as far as the line of greatest contour, preferably extending beyond this, preferably as far as the gum/tooth junction, but without defining an undercut surface. Preferably, these walls extend beyond the contact zone with the one or more adjacent teeth. The adhesive bonding surface is thus advantageously increased.

Preferably, the designing of the ring model is assisted by computer, in particular in order to determine material thicknesses that are adapted to the mechanical stresses in the service position of the ring.

In step c), the operator manufactures the ring 2, preferably by means of a 3D printer, such that it conforms to the ring model created in step b).

Preferably, the thickness and the nature of the material of the shell are defined in such a way that the ring is not elastically deformable and in particular in such a way that it is not deformable by hand. It can in particular me made of a material chosen from among the alloys cobalt-chromium, titanium, nickel-titanium, titanium-niobium or all biocompatible metal alloys. The fixation ring is not intended to replace all or part of the fixation tooth, not even temporarily. Its thickness may be substantially constant.

In a preferred embodiment, the thickness of the bottom of the ring is variable, preferably in order to decrease progressively in the direction of its center, preferably in such a way as to be substantially zero at the edge of the hole 16.

The use of 3D printing for manufacturing the ring advantageously makes it possible to obtain a roughness of the inner surface that is adapted to efficient adhesive bonding, without any other treatment operation.

The manufacture by means of a 3D printer is advantageously very rapid. In one embodiment, the ring is produced immediately after step a) and step b), which makes it possible to speed up the orthodontic treatment.

In one preferred embodiment, the connecting crosspiece is manufactured, by means of a 3D printer, at the same time as the ring. Preferably, the connecting crosspiece and several dental rings and/or hooks are manufactured at the same time by means of a 3D printer. This advantageously facilitates placement on the dental arch.

It is also preferable that the one or more accessories are also manufactured, by means of a 3D printer, at the same time as the ring.

In one embodiment, a groove is machined in the ring such that a connecting member can be accommodated therein.

Preferably, the groove is defined in accordance with the treatment that is to be applied to the patient. In particular, the orientation of the groove is preferably defined according to the action that is to be exerted specifically on the teeth of the patient.

The manufacture thus combines additive printing for the ring, then subtractive manufacture, preferably by machining, for the groove.

Preferably, the orientation of the groove contains third-order information that will be expressed by means of an orthodontic archwire that has a cross section substantially complementing that of the groove, preferably a square or rectangular cross section. The more the cross section of the orthodontic archwire is similar to the cross section of the groove, the more the third-order information will be clear.

In step d), the operator preferably polishes the outer surface $14_e$ of the ring. Advantageously, the outer surface $14_e$ thus has a roughness that is less than the inner surface $14_i$, closer to the roughness of a tooth.

In one preferred embodiment, the inner surface is not polished. The rough microstructure of the inner surface $14_i$, resulting from the 3D printing, is thus preserved.

In one embodiment, the roughness is increased by applying laser radiation to the inner surface in order to create micro-reliefs and thus to increase the roughness.

In order to fix the ring, the orthodontist traditionally applies glue or a sealing cement to the inner surface $14_i$ of the ring and/or to the fixation tooth. All of the glues or sealing cements that are used traditionally in orthodontics can be used.

When the ring extends beyond the line of greatest contour of the fixation tooth without internally defining an undercut surface, its inner surface is at a distance from the undercut surface of the fixation tooth, beyond this line (in the direction of the gum). Preferably, the quantity of glue or sealing cement is adjusted in order to fill the undercut region which, beyond the line of greatest contour, extends between the inner surface of the ring and the surface of the fixation tooth.

The orthodontist then applies the ring to the fixation tooth. The shape of the inner surface $14i$, identical to that of the fixation tooth, permits precise and rapid fixation, without exerting great force on the fixation tooth. The roughness of the inner surface $14_i$ improves the adhesion.

After placing a second ring (or an orthodontic bracket), not shown, on a second fixation tooth, the orthodontist positions the connecting member 20 in the fasteners of the two rings, then activates these ring fasteners in order to ensure a rigid connection between the connecting member 20 and each of the two rings.

Depending on the clinical situation, the second ring can be replaced by an orthodontic bracket.

The connecting member 20 can then ensure that a tensile or compressive force is exerted on the fixation teeth by the rings in order to ensure movements in accordance with the desired orthodontic treatment.

The inventors have found that a ring according to the invention permits very effective anchoring on the fixation tooth, even if the ring is not compressed by an adjacent tooth and does not have a wall bearing on an undercut surface of the fixation tooth.

The method described in detail above can also be used to manufacture the active member, and in particular the connecting member or a crosspiece.

Preferably, the three-dimensional digital model of the active member is designed according to the treatment that is to be applied. In particular, it is preferably made of a shape-memory material and designed according to the forces that are to be exerted on the teeth of the patient, these forces being dependent on the specific configuration of the teeth of the patient.

The active member, in particular when it replaces an actuator of a conventional expander, can be made of a shape-memory material, but also of a polymer material called a "4D" material, that is to say a material that can be programmed to deform by application of a temperature increase arising from the service position, that is to say an increase of temperature between 20° C. (ambient temperature) or a temperature less than 20° C. and about 37° C.

In the case of an expander, the material of the active member, preferably the material of the expander, is preferably chosen such that, after activation on account of a stimulus, preferably on account of the temperature increase, it tends to widen the dental arch, which is the traditional function of an expander.

Preferably, the active member has or even consists of a material that is retractable or expansible under the effect of said temperature increase, preferably a polymer material. Preferably, the modification of the volume of the active member under the effect of this temperature increase is greater than 1%, 2%, 5%, 8%, 10%, 20% or even 50% of the initial volume, prior to said temperature increase.

The member can be configured to deform progressively or instantly under the effect of said temperature increase.

Generally, the stimulus for activating the active member can be chosen from the group consisting of radiation, in particular light radiation, infrared radiation, ultraviolet radiation or sound radiation, a change of the humidity and/or of the acidity and/or of the temperature and/or of the chemical composition of the environment of the member, application of an electric current and/or of an electric voltage and/or of a magnetic field, and combinations of these.

In one embodiment, the stimulus is applied for a period of less than 1 hour, less than 30 minutes, less than 60 seconds, less than 30 seconds, less than 10 seconds, less than 5 seconds, less than 1 second.

The placement of a dental device according to the invention does not pose any particular difficulty.

In one embodiment, the dental device is manufactured, by 3D printing, with a support which keeps all the bracket members in relative positions corresponding to their relative service positions. The bracket members can thus be fixed to the teeth, preferably by adhesive bonding, simultaneously and with great precision. In one embodiment, the support is printed in the same material as the bracket members. It preferably forms a one-piece assembly with these. After fixation to the teeth, the support can be disconnected from the bracket members by grinding the junctions between the support and the bracket members.

In one embodiment, the support, preferably at least one said junction, is flexible, which facilitates the placement of the dental device, particularly if a bracket member defines a pressure surface intended to be in contact with an undercut tooth surface. The flexibility can be adjusted by modifying the cross section of the junctions.

As will now be clear, the invention permits rapid orthodontic treatment, minimizing the number of visits to the orthodontist, in particular for fitting separators and then trying out rings.

It also permits the manufacture of a tailor-made dental device, and in particular a combined multi-bracket aligning and leveling device (orthodontic brackets+rings).

The individual customization of the dental device also makes it possible to reduce the finishing time and thereby shorten the overall duration of treatment.

Finally, the shaping and fitting of the bracket members is painless.

Of course, the invention is not limited to the embodiments described and shown, which have been provided solely for illustrative purposes.

In particular, a bracket member, and in particular a ring, can extend over several fixation teeth, in particular in order to define a substantially stationary point for attachment of the connecting member.

The dental device can have several active members (crosspieces and/or connecting members) fixed in respective sheaths or grooves, which sheaths or grooves can be vestibular or lingual. In one embodiment, the device has a first active member, fixed to first bracket members, at the level of the palate, in order to create the palatal expansion or to maintain same, and a second active member, in the form of an orthodontic archwire, fixed to second bracket members, preferably grooves, in order to modify the position of the teeth. It is thus possible to combine two treatment actions: palatal expansion and alignment of the teeth.

The invention claimed is:

1. A method comprising a manufacturing and a fixing of a dental expander having:
 a first bracket member intended to be fixed to a first fixation tooth of a dental arch of a patient;
 a second bracket member intended to be fixed to a second fixation tooth of the dental arch of the patient;
 a transversal active member rigidly connected to the first and second bracket members and configured such that, in a service position in which the expander is fixed to said dental arch, it exerts an action that laterally widens said dental arch;
 the first bracket member being a dental fixation ring having a bottom intended to be placed on an occlusal surface of the first fixation tooth, and a lateral wall intended to encircle said first fixation tooth, the lateral wall being composed of a lingual wall, a vestibular wall and first and second proximal walls,
said manufacturing having the following successive steps:
 a) a three-dimensional digital model of a dental arch having the first and second fixation teeth, or "arch model", is generated, by means of an optical scanner;
 b) the arch model and a treatment to be applied to the patient are used as a basis for generating:
  a three-dimensional digital model of the first bracket member, the model of the first bracket member having an inner surface that substantially reproduces a part of the surface of the first fixation tooth, and
  a three-dimensional digital model of the second bracket member, the model of the second bracket member having an inner surface that substantially reproduces a part of the surface of the second fixation tooth, and/or
  a three-dimensional digital model of the active member;
 c) the model of the first bracket member is used as a basis for manufacturing said first bracket member, and/or the model of the second bracket member is used as a basis for manufacturing said second bracket member, and/or the model of the active member is used as a basis for manufacturing said active member the active member being made integral with the first and second bracket members so as to form a one-piece assembly;
 a fixing of said dental fixation ring on the teeth of the patient with glue or with a sealing cement applied to an inner surface of the dental fixation ring and/or to the first fixation tooth receiving said dental fixation ring,
in which the active member has a shape-memory material or a polymer material deformable under the effect of a stimulus,
the stimulus for activating the active member being chosen from the group consisting of light radiation, infrared radiation, ultraviolet radiation, sound radiation, a change of the humidity and/or of the acidity and/or of the temperature and/or of the chemical composition of the environment of the member, and
the shape of the active member and the shape-memory properties being determined according to the treatment that is to be applied to the patient,
in which, in step b), the model of the first bracket member is defined in such a way that the dental fixation ring resulting from step c) does not have an undercut region.

2. The method as claimed in claim 1, in which the stimulus for activating the active member is a temperature increase resulting from the expander being placed in the service position.

3. The method as claimed in claim 1, in which, after step c), the shape memory of the active member is deactivated by cooling before the expander is fixed in the mouth of the patient, the shape-memory material being chosen such that the body temperature of the patient activates said shape memory.

4. The method as claimed in claim 1, in which, in step c), the active member is manufactured from a material identical to that of the first bracket member and/or of the second bracket member.

5. The method as claimed in claim 1,
 in which, in step b), the model of the first bracket member is defined in such a way that the dental fixation ring resulting from step c) extends beyond the line of greatest contour of the first fixation tooth without defining an undercut region.

6. The method as claimed in claim 5, in which the model of the first bracket member is defined in such a way that the bottom of the dental fixation ring has at least one hole passing through it.

7. The method as claimed in claim 6, in which the hole is defined in such a way that, in the service position, the bottom of the dental fixation ring does not even partially cover the mastication surface of the first fixation tooth.

8. The method as claimed in claim 1, said method having, after step c), a step d) in which at least part of the outer surface of the bracket member is polished, without the inner surface of the bracket member being polished.

9. The method as claimed in claim 5, in which, in step b), the model of the first bracket member is defined in such a way that the height of the lingual wall and/or of the vestibular wall is greater than the height of the first proximal wall and/or of the second proximal wall.

10. The method as claimed in claim 9, in which, in step b), the model of the first bracket member is defined in such a way that the lingual wall and/or the vestibular wall extend, from the bottom, beyond the line of greatest contour of the first fixation tooth.

11. The method as claimed in claim 5, in which, in step b), when the first proximal wall is intended to extend, in the service position, between the first fixation tooth and an adjacent tooth in contact with the first fixation tooth via a contact zone, the model of the first bracket member is defined in such a way that, in said service position, the first proximal wall does not reach said contact zone.

12. The method as claimed in claim 1, in which, in step c), the first and second bracket members and the active member are manufactured by 3D printing.

13. The method as claimed in claim 1, in which the dental fixation ring is made of a material chosen from among the alloys cobalt-chromium, titanium, nickel-titanium, titanium-niobium or all biocompatible metal alloys.

14. The method as claimed in claim 1, in which the roughness of the inner surface is increased by applying laser radiation to said inner surface in order to create micro-reliefs.

15. The method as claimed in claim 1, in which the active member consists of said shape-memory material or consists of said polymer material deformable under the effect of a stimulus.

16. The method as claimed in claim 1, in which, after step c), the glue or the sealing cement is applied to the inner surface of the dental fixation ring.

17. The method as claimed in claim 1, in which the quantity of glue or sealing cement is adjusted in order to fill a region which, beyond the line of greatest contour, extends between the inner surface of the dental fixation ring and the surface of the first fixation tooth.

\* \* \* \* \*